United States Patent [19]

Norton

[11] 4,113,763
[45] Sep. 12, 1978

[54] PROCESS FOR CYANOHYDRIN ESTERS

[75] Inventor: Richard V. Norton, Wilmington, Del.

[73] Assignee: Suntech, Inc., Wayne, Pa.

[21] Appl. No.: 776,452

[22] Filed: Mar. 10, 1977

[51] Int. Cl.$^2$ ............................................. C07C 121/66
[52] U.S. Cl. .................................................. 260/465 D
[58] Field of Search .................................... 260/465 D

[56] References Cited

U.S. PATENT DOCUMENTS

| | | | |
|---|---|---|---|
| 3,787,477 | 1/1974 | Mathews | 260/465 F |
| 3,835,176 | 9/1974 | Matsuo et al. | 260/465 D |

FOREIGN PATENT DOCUMENTS 2,231,312  1/1973  Fed. Rep. of Germany.

OTHER PUBLICATIONS

Michael et al., Ber., vol. 25, pp. 1678–1684, (1892).
Francis et al., J. Chem. Soc., 95, pp. 1403–1409, (1909).
Fisher et al., J. Org. Chem., 24, pp. 1650–1654, (1959).

*Primary Examiner*—Dolph M. Torrence
*Attorney, Agent, or Firm*—J. Edward Hess; Donald R. Johnson; Paul Lipsitz

[57] ABSTRACT

A single step, non-aqueous process for the preparation of aromatic cyanohydrin esters by reacting together an aromatic aldehyde, an alkali metal cyanide, and a lower aliphatic acid anhydride. The cyanohydrin esters are useful as intermediates to potent insecticides.

4 Claims, No Drawings

PROCESS FOR CYANOHYDRIN ESTERS

This invention relates to a novel process for making aromatic cyanohydrin esters by a one-step, non-aqueous process and involves the reaction of an aromatic aldehyde, an alkali metal cyanide and a lower aliphatic acid anhydride.

The conversion of benzaldehyde cyanohydrin to a cyanohydrin acetate was reported as early as 1892. Michael and Jeanpretre [Ber. 25, 1678 (1892)] reacted mandelonitrile and acetic anhydride in equal molar quantities and obtained a nearly quantitative yield of cyanohydrin acetate.

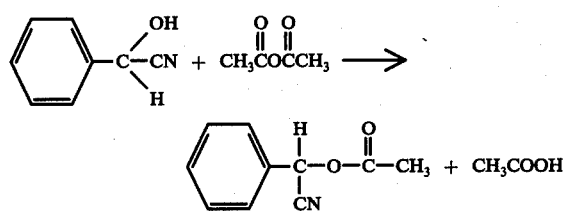

However, in this sequence the cyanohydrin is necessarily prepared first by a reaction of aldehyde with aqueous HCN in the presence of a base. It is also known to prepare the cyanohydrin in high yields by the process disclosed in U.S. Pat. No. 3,787,477 where aldehyde, sodium cyanide and acetic acid are reacted in an aqueous system:

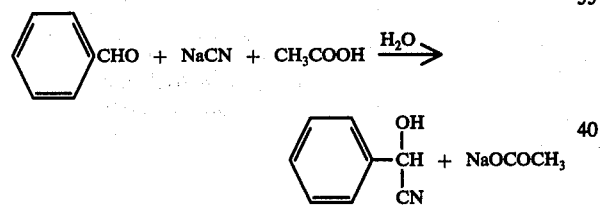

Also known is the use of acyl chlorides for formation of cyanohydrin esters. Francis and Davis [J. Chem. Soc., 95 1403 (1909)] found that benzaldehyde readily gave a quantitative yield of benzylmandelonitrile when treated with benzoyl chloride in the presence of an aqueous solution of potassium cyanide.

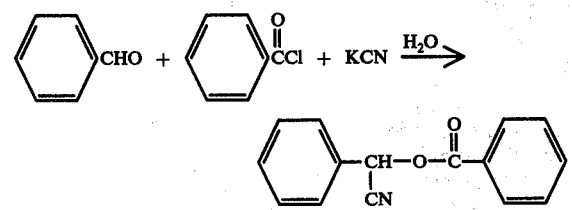

A number of other derivatives were similarly prepared from phthaloyl chloride, benzenesulfonyl chloride and anisoyl chloride.

Insecticides of the pyrethroid type have been prepared by reaction of an acyl chloride of the pyrethrin with an aldehyde in the presence of sodium cyanide (Ger. Offen No. 2,231,312); e.g.

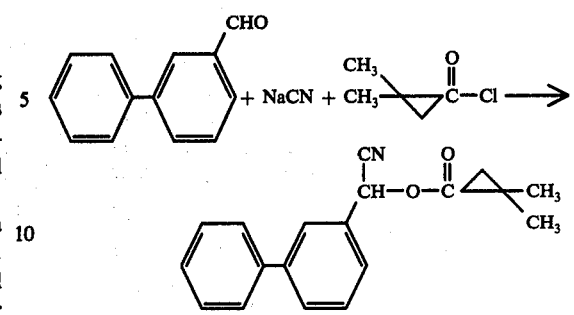

Making and using an acetyl chloride, however, is difficult, hazardous and expensive. The present invention enables a cyanohydrin acetate to be easily obtained and such compound is readily converted by ester-interchange with a pyrethrin ester to the potent insecticide product; e.g.

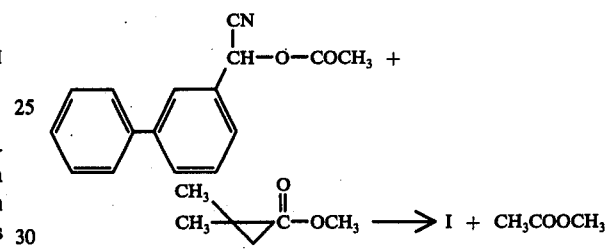

The process of this invention provides a novel, one step preparation of acyl derivatives of aldehyde cyanohydrins and substituted derivatives having the structure:

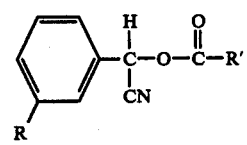

Where R is hydrogen or an alkyl or aryl substituent, preferably a hydrocarbon group having from one to ten carbon atoms and R' is an aliphatic group of from one to about four carbon atoms.

This method is particularly useful because a separate and discrete step to form the cyanohydrin is avoided, and the necessity of handling HCN is also eliminated. The use of acyl halides is also unnecessary thus avoiding a costly conversion of anhydrides to acyl chlorides. The simple aliphatic anhydride reactant serves as a solvent for the reaction providing ease of operation.

The chemical reaction of the process may be illustrated as follows:

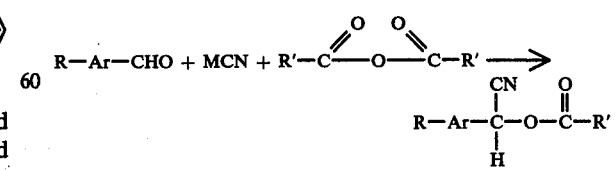

Ar in the above equation is an aromatic group, preferably of the benzene and naphthalene series and R is hydrogen or an alkyl, aryl or cycloalkyl group, preferable hydrocarbon of one to ten carbon atoms although it may contain an inert substituent such as halogen, alkyl, alkoxy and cyano. M is an alkali metal, the cyanide, behind preferably NaCN or KCN, the latter being most preferred. R' is a lower aliphatic group, preferably methyl. Examples of useful aldehydes are benzaldehyde, tolualdehyde, naphthaldehyde, m-phenoxybenzaldehyde, and p-phenoxy benzaldehyde. The useful anhydrides will be acetic anhydride, propionic acid anhydride, butyric acid anhydride and the like although acetic anhydride will be preferred because of availability and cost.

The reaction proceeds most effectively when the aldehyde and cyanide reactants are used in an at least approximate equimolar basis: i.e., about one mole of metal cyanide per mole of aldehyde reactant dissolved in an excess of acetic anhydride. Generally, the use of amounts of cyanide ranging from 1.0 to 2 moles per mole of benzaldehyde or substituted benzaldehyde with 10 moles of anhydride is effective. In the preferred reaction, a slight molar excess of cyanide over the amount of aldehyde reactant and, in turn a ten fold molar excess of anhydride over the cyanide is employed. The product is conveniently recovered by extraction into a solvent, washing with water, removing the salts and distillation of the organic layer.

The reactive conditions include temperatures from about 0° to 50°C and preferably 35°-40° C with external cooling or use of a refluxing low boiling solvent to remove the heat of reaction. Suitable media are n-pentane, butane, diethyl either and fluorocarbons. Temperatures above 50° C (say up to about 100° C) are operable, but yields are reduced significantly. The system must be essentially anhydrous to avoid conversion of the acetic anhydride to free acid. The reaction should be carried out by a preferred order of addition. The metal cyanide is added to the fluid aldehyde or aldehyde dissolved in an appropriate solvent. If aldehyde is added to anhydride then the competing reaction to produce benzylidene diacetates occurs. To the stirring slurry, the anhydride is then slowly added in order to minimize the exotherm. Alternatively, the metal cyanide may be dissolved in the anhydride and the aldehyde added to it. The vigorous exothermic reaction is controlled by cooling and rate of reactant addition. The reactants are then maintained at about 40° for a time to optimize yield of product as determined by vapor phase chromatographic analysis.

That the cyanohydrin acetate is formed with acetic anhydride and KCN is indeed unexpected since the normal reaction of aldehydes with anhydrides is to form benzylidine diacetates:

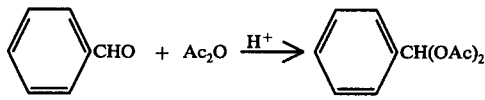

In order to further illustrate the process of the invention the following examples are given:

EXAMPLE 1

No KCN - Benzylidine Diacetate

Benzaldehyde (29.6g, 0.28 moles) was added cautiously with stirring to acetic anhydride (55g. 0.54 moles) containing 1 drop of polyphosphoric acid. The vigorous exothermic reaction was tempered by cooling and the rate of benzaldehyde addition. The temperature was not allowed to exceed 60° C. After setting aside for 2 hours at 25° C, the solution was washed with water and the aqueous system extracted with toluene solution being dried with anhydrous sodium carbonate.

Distillation yielded benzylidine diacetate in 80% yield, bp 107°–115° C/0.4–0.5 mm Hg. Literature: 154°/20 mm, J. Chem. Soc. 1384 (1955).

EXAMPLE 2

Preparation of Cyanohydrin Acetate

Powdered KCN (75g, 1.15 moles) was slurried in benzaldehyde (106g, 1 mole) at room temperature in a three necked flask fitted with a thermometer, $N_2$ sweep and paddle stirrer. Acetic anhydride (1.05 moles) containing 1% acetic acid was cautiously added dropwise to the reactant slurry. An immediate exothermic reaction ensued reminiscent of the benzylidine diacetate formation. The anhydride addition took about 1½ hours to add due to the severe exotherm up to 71% reaction. Extraction of the system with water, followed by drying of the toluene extract of the aqueous system and distillation gave a 60% yield of cyanohydrin acetate.

A second experiment wherein the exotherm reached 75° C lowered the yield to 40% and gave an increase in the benzylidine diacetate side product.

As shown by example 1, the benzylidine diacetate formation occurs under essentially identical external conditions as the cyanohydrin acetate formation occurs. It was anticipated that a modest yield of cyanohydrin acetate would be formed but a yield in excess of 60% without formation of benzylidine diacetate is entirely unexpected.

EXAMPLE 3 m-phenoxybenzaldehyde (10 g) was added to a slurry of KCN (5 g) dissolved in 50 cc of acetic anhydride. There was a modest exotherm and while stirring the slurry was warmed at 40° for 7 hours. VPC analysis shows an 80% conversion to the cyanohydrin acetate and 10% conversion to the benzylidine diacetate.

The cyanohydrin acetate obtained above has the structure

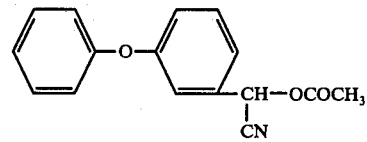

and when transesterfied with the methyl ester of 2,2-dimethyl-3-2',2'-dichlorovinyl-cyclopropane-1-carboxylic acid yieldsthe potent insecticide known as NRDC-149.

The invention claimed is:

1. A process for making aromatic cyanohydrin esters which consists of adding a lower aliphatic acid anhydride under essentially anhydrous conditions to a mixture of an alkali metal cyanide and an aromatic aldehyde of the structure R-ArCHO, where Ar is a member of the benzene or naphthalene series and R is hydrogen or lower alkyl, said aromatic aldehyde and said cyanide being used in approximate equimolar amounts and said anhydride being used in a molar excess and controlling the exothermic reaction to maintain a temperature between about 0° and 50° C.

2. The process of claim 1 where the aldehyde is benzaldehyde and the anhydride is acetic anhydride.

3. The process of claim 2 where the alkali metal cyanide is potassium cyanide.

4. The process of claim 1 where the aldehyde is benzaldehyde, the anhydride is acetic anhydride and the cyanide is potassium cyanide.

* * * * *